United States Patent

Schulz

[19]

[11] Patent Number: 5,923,722
[45] Date of Patent: Jul. 13, 1999

[54] X-RAY DIAGNOSTIC APPARATUS WITH CONTROL OF X-RAY EMISSION DEPENDENT ON THE AFTERGLOW IN THE SOLID-STATE DETECTOR

[75] Inventor: Reiner Schulz, Dormitz, Germany

[73] Assignee: Siemens Aktiengesellschaft, Munich, Germany

[21] Appl. No.: 08/904,254

[22] Filed: Jul. 31, 1997

[30] Foreign Application Priority Data

Aug. 5, 1996 [DE] Germany .................. 196 31 624

[51] Int. Cl.$^6$ ..................... H05G 1/64
[52] U.S. Cl. ................. 378/98.8; 378/98.7
[58] Field of Search .................. 378/98.7, 98.8, 378/98.11, 98.12, 207

[56] References Cited

U.S. PATENT DOCUMENTS

| | | | |
|---|---|---|---|
| 5,452,338 | 9/1995 | Granfors et al. ............ | 378/207 X |
| 5,530,238 | 6/1996 | Muelenbrugge et al. ...... | 378/98.8 X |
| 5,668,375 | 9/1997 | Petrick et al. ............... | 378/98.8 X |
| 5,771,272 | 6/1998 | Berger et al. ................. | 378/207 |

FOREIGN PATENT DOCUMENTS

| | | |
|---|---|---|
| 0 642 264 | 3/1995 | European Pat. Off. . |
| 1 489 345 | 10/1977 | United Kingdom . |

Primary Examiner—David P. Porta
Attorney, Agent, or Firm—Hill & Simpson

[57] ABSTRACT

An X-ray diagnostic apparatus has at least one beam transmitter which emits an X-ray beam acquired by at least one solid-state detector with image points arranged in the form of a matrix, and at least one correction unit that acquires the image signals, produced by the solid-state detector, of the current bright image exposure of a subject to be examined, and acquires the any afterglow signals which may be present from at least one dark image exposure. The correction unit controls the beam transmitter dependent on the presence of afterglow signals and/or the intensity of the afterglow signals, and, if necessary, corrects the image signals of the current bright image exposure.

13 Claims, 4 Drawing Sheets

X-RAY DIAGNOSTIC APPARATUS WITH CONTROL OF X-RAY EMISSION DEPENDENT ON THE AFTERGLOW IN THE SOLID-STATE DETECTOR

BACKGROUND OF THE INVENTION

1. Field of the Invention

The present invention is directed to an X-ray diagnostic apparatus of the type having a solid-state radiation detector.

2. Description of the Prior Art

An X-ray diagnostic apparatus of this type is known e.g. from European Application 0 642 264. In this known apparatus, the X-ray beams produced by a beam transmitter are acquired by a solid-state detector with image points arranged in the form of a matrix. Due to the time behavior of the scintillator and the photodiodes after switching off the X-ray radiation, these detectors, based on amorphous silicon, produce afterglow signals, which lead to what are referred to as "ghost" or "phantom" images. In the current X-ray exposure, called the bright image exposure in the following, a residuum of the previous image or images can thus be seen. This effect is very disturbing, and in the X-ray diagnostic apparatus according to European Application 0 642 264 it is corrected by calculating the phantom image still present in the current bright image from previous bright images, and subtracting it. This method is relatively imprecise, and fails in cases of overdriven points (blooming) in the bright image, since the initial brightness value for the calculation of the decay of the afterglow signals is not known.

British specification 1 489 345 discloses a method for the removal of afterglow effects in which bright and dark images are exposed and are mutually balanced (subtracted) in order to remove the disturbance.

It is an object of the present invention to provide an X-ray diagnostic apparatus of the general type described above that has an improved phantom image characteristic.

The above object is achieved in an X-ray diagnostic apparatus according to the invention having at least one beam transmitter, which emits an X-ray beam that is acquired by at least one solid-state detector with image points arranged in the form of a matrix, and at least one correction unit, which acquires the image signals produced by the solid-state detector, of the current bright image exposure of a subject to be examined. In addition, the correction unit acquires any afterglow signals which may be present from at least one dark image exposure. Only the current afterglow can be seen in these dark images. The correction unit controls the beam transmitter dependent on the presence of afterglow signals and/or dependent on the intensity of the afterglow signals. If necessary, the image signals of the current bright image exposure are corrected in the correction unit. The corrected image signals of the current bright image exposure can then be further processed in a known way (e.g. filtering, hard copy, archiving, feeding into networks, etc.).

The inventive X-ray diagnostic apparatus does not emit an X-ray pulse with a bright image being exposed in every possible time interval; rather, at least one dark image is intermittently exposed. From these dark image exposures, in which only the current afterglow can be seen, the afterglow portion in the bright image exposures can be determined and eliminated.

Due to the inventive measure of determining the afterglow signals from at least one dark image exposure, low-dose exposures (transillumination) after preceding high-dose exposures (bright image exposures that are stored) are also possible without difficulty.

DESCRIPTION OF THE PREFERRED EMBODIMENT

Figure 1:
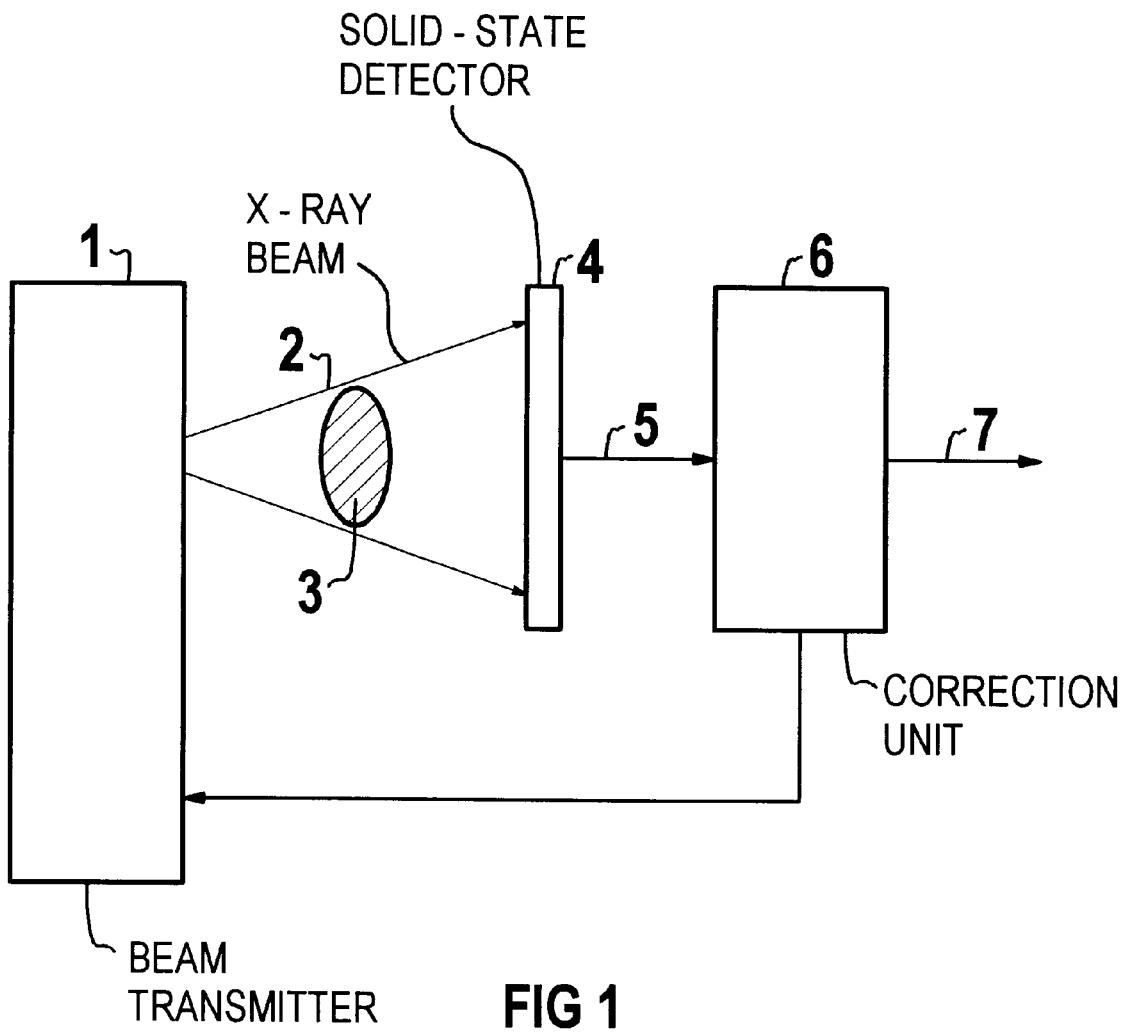
FIG. 1 shows an exemplary embodiment of the inventive X-ray diagnostic apparatus.

In FIG. 1, a beam transmitter 1 emits X-rays 2 that penetrate a subject 3 to be examined. After penetrating the subject 3 to be examined, the X-rays 2 are detected in a solid-state detector 4. The image signals 5 produced by the solid-state detector 4 during this bright image exposure are supplied to a correction unit 6. The correction unit 6 controls the beam transmitter 1 dependent on the presence of afterglow signals and/or dependent on the intensity of the afterglow signals. The afterglow signals are determined from at least one dark image exposure containing only the current afterglow. If required, the image signal 5 is corrected in the correction unit 6. The corrected image signals 7 can then be further processed (e.g. filtering, hard copy, archiving, feeding into networks, etc.).

Figure 2:
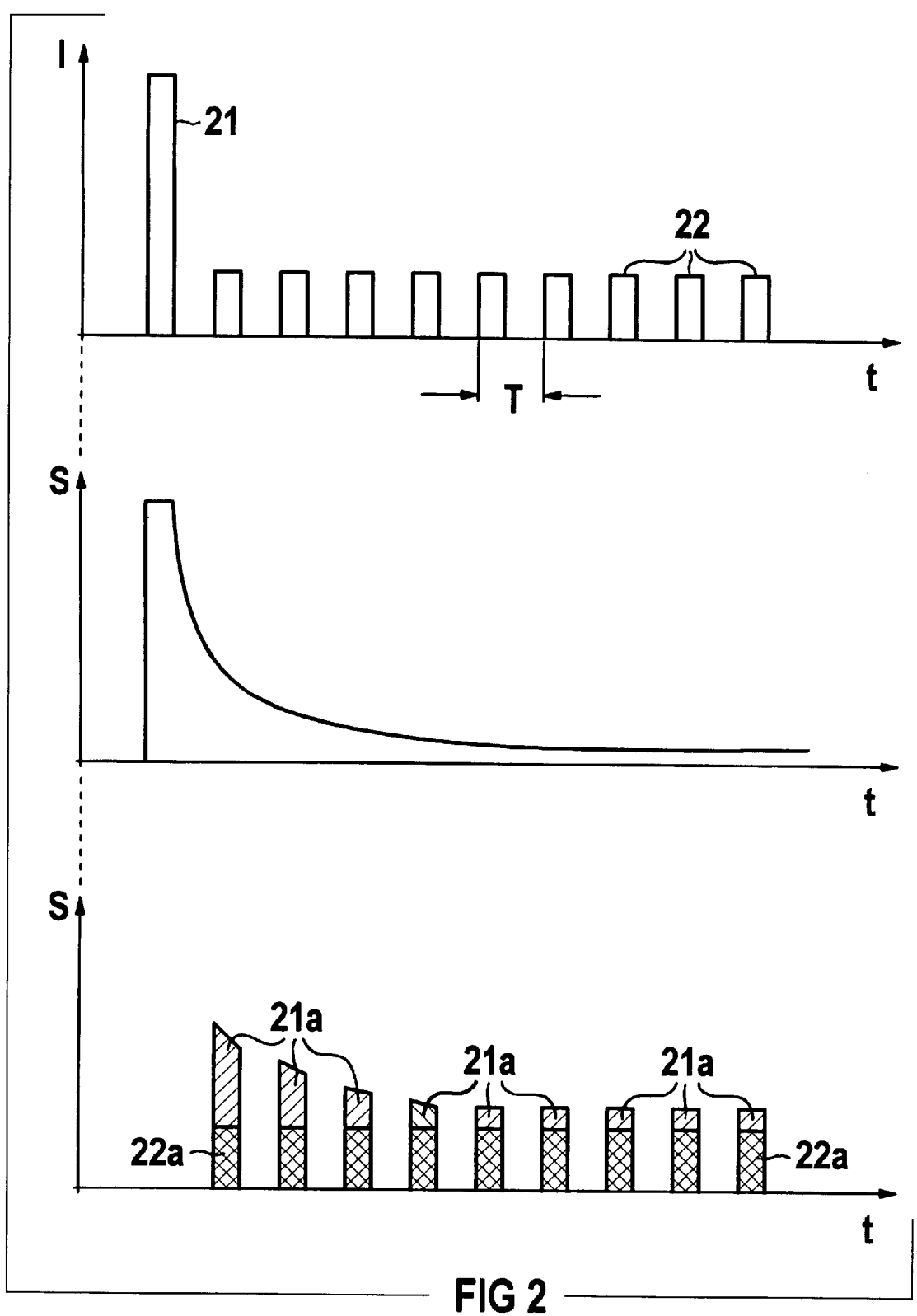
FIGS. 2–4 show examples for the chronological sequence of different X-ray pulses, wherein l designates the intensity of the X-ray impulse, S designates its signal and t designates time.

FIG. 2 illustrates the timing schema according to which the X-ray pulses are normally applied. After, for example, a high-intensity X-ray pulse, called a high-dose impulse 21 in the following, there follows a series of X-ray pulses of lower intensity, called low-dose impulses 22 below (FIG. 2, top). The signal of the high-dose impulse 21 (FIG. 2, center) deviates more or less strongly from the ideal signal curve (rectangular signal), due to the physical constitution of the solid-state detector 4. The detected overall signals (FIG. 2, bottom) thus have a portion 21a that comes from the high-dose pulse 21 and a portion 22a that comes from the low-dose pulse 22. The portion 21a from the high-dose pulse 21 must be eliminated in order to obtain the corrected image signal $S^*_n$ (designated 7 in FIG. 1). In this case, the corrected image signal $S^*_n$ receives only the portions 22a of the low-dose pulse. The portions 21a of the high-dose pulse 21 are responsible for the ghost or phantom images in the overall signal.

In the X-ray diagnostic apparatus shown in FIG. 1, it is not the case that an X-ray impulse is applied and a bright image exposed in every possible time interval T; rather, dark images are intermittently exposed. In these dark image exposures, only the current afterglow that arises due to the deviation of the real signal curve from the ideal signal curve can be seen. From these dark image exposures, the afterglow portion in the bright image exposures can be determined and eliminated.

Figure 3:
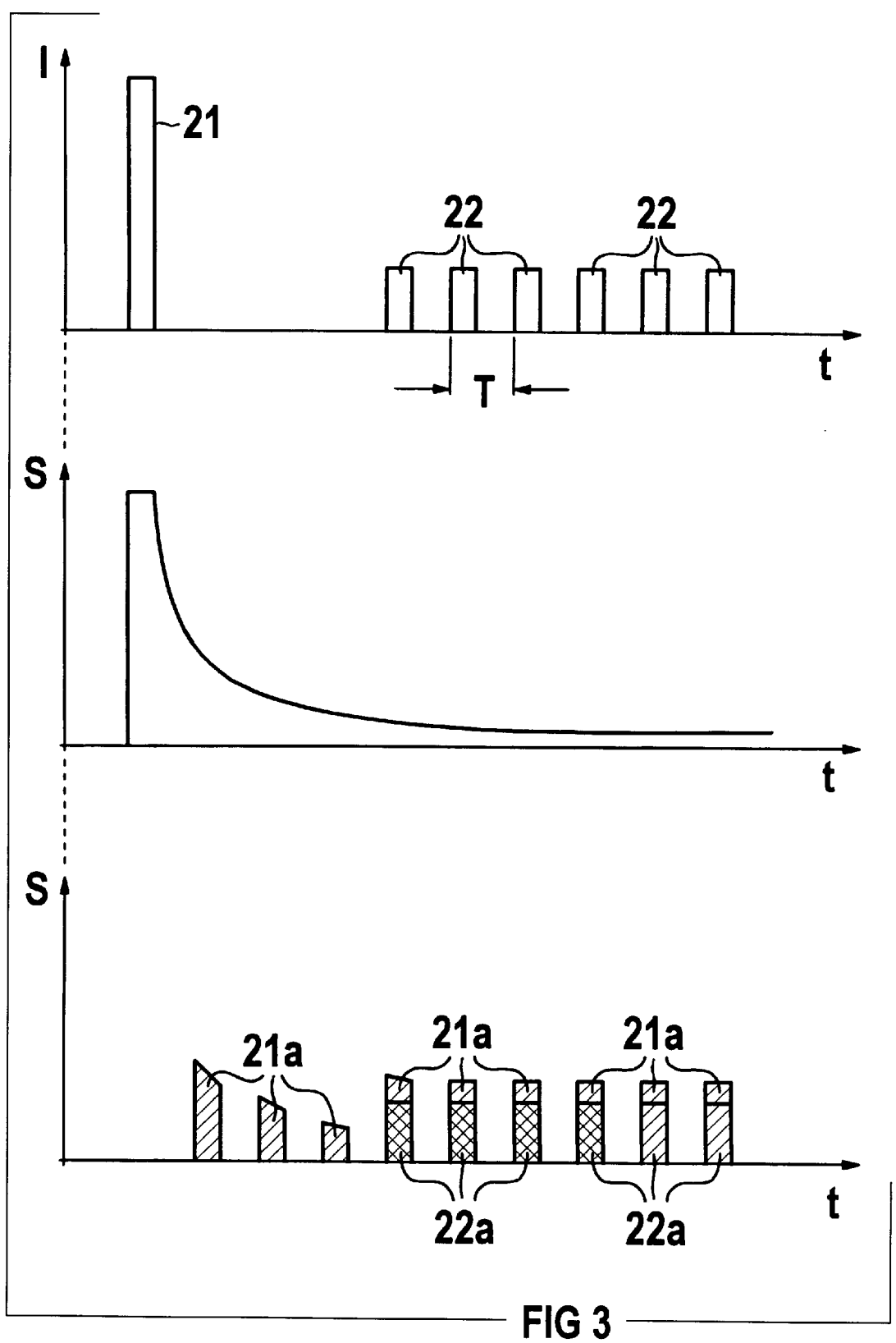

The dark images can be obtained according to different patterns. It is advantageous to expose a series of dark images first after the high-dose impulse 21 (FIG. 3). If the decay of the portions 21 a of the high-dose pulse 21 is very strong, a part of the dark image exposures can be ignored. The frequency of the dark image exposures can remain constant or can change with time; e.g., if the afterglow signal (phantom image) of the high-dose exposure still decreases strongly it can, for example, be useful to expose every other image as a dark image, then later every third, fourth, etc. image, until the phantom image portion (afterglow signals of a high-dose pulse) is no longer visible, and a phantom image correction is no longer required.

There are various possibilities for the determination of the afterglow signals, i.e. of the afterglow portion to be removed from the bright image exposure. Thus, the afterglow portions can be determined from the dark image exposures, e.g. by average value formation and/or taking into account the decay behavior.

Thus, for example, from at least two previous dark image exposures the average value can be formed and removed from the respective bright image. As an alternative to the arithmetic formation of the average value, the afterglow portion to be removed can be determined by means of average value formation, weighted in sliding fashion, from several previous dark image exposures.

Figure 4:
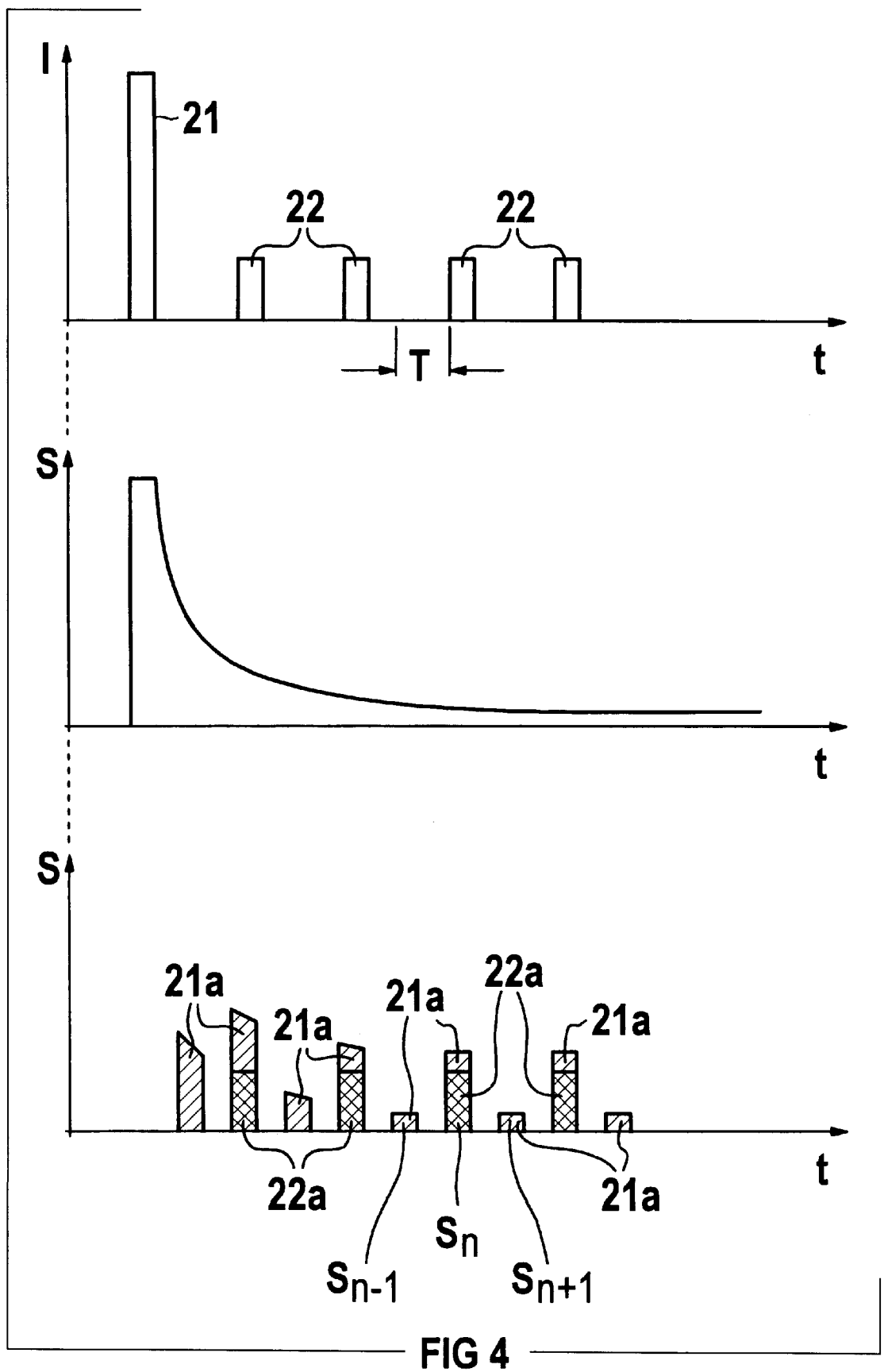

A further alternative is the calculation of an average value from at least one previous and one subsequent dark image exposure (FIG. 4). This average value is then removed from the bright image exposure as the afterglow portion. The corrected signal $S^*_n$ then results as $$S^*_n = S_n - (S_{n-1} + S_{n+1})/2.$$

The afterglow signal in the form of the average value (afterglow portion) can additionally be reduced by a portion corresponding to the further decay, so that the average value obtained from the measured afterglow portions corresponds to the afterglow portion at the time of the bright image exposure. Alternatively, the further decay can be calculated from the series of dark images exposed directly after the high-dose pulse, and can be removed from the following bright image exposures.

Although the present invention has been described with reference to a specific embodiment, those of skill in the art will recognize that changes may be made thereto without departing from the scope and spirit of the invention as set forth in the appended claims.

I claim as my invention:

1. An X-ray diagnostic apparatus comprising:
   an X-ray source which emits an X-ray beam;
   a solid-state radiation detector on which said X-ray beam is incident, said solid-state radiation detector having a plurality of image points arranged in a matrix and exhibiting afterglow; and
   correction means which receives image signals from said solid-state radiation detector produced when said X-ray beam is incident on said solid-state radiation detector and for acquiring a dark signal from said solid-state radiation detector without any X-rays incident thereon, and for controlling emission of said X-ray beam by said X-ray source dependent on any signals produced by said afterglow contained in said dark signal and, if necessary, for correcting said image signal dependent on said dark signal.

2. An X-ray diagnostic apparatus as claimed in claim 1 wherein said correction means comprises means for controlling said X-ray source and for correcting said image signals dependent on a presence of afterglow signals in said dark signal.

3. An X-ray diagnostic apparatus as claimed in claim 1 wherein said correction means comprises means for controlling said X-ray source and for correcting said image signals dependent on an intensity of afterglow signals in said dark signal.

4. An X-ray diagnostic apparatus as claimed in claim 1 comprising means for generating said image signal and said afterglow signal in digital form.

5. An X-ray diagnostic apparatus as claimed in claim 1 comprising means for producing said dark signal before said image signal.

6. An X-ray diagnostic apparatus as claimed in claim 1 comprising means for producing said dark signal after said image signal.

7. An X-ray diagnostic apparatus as claimed in claim 1 comprising means for producing said dark signal before and after said image signal.

8. An X-ray diagnostic apparatus as claimed in claim 1 wherein said correction means comprises means for obtaining a plurality of dark signals and means for forming an average value of said plurality of dark signals, and wherein said correction means comprises means for controlling said X-ray source and for correcting said image signal dependent on said average.

9. An X-ray diagnostic apparatus as claimed in claim 8 wherein said means for forming an average value comprises means for forming an arithmetic average value.

10. An X-ray diagnostic apparatus as claimed in claim 8 wherein said means for forming an average value comprises means for forming an average value with the respective dark signals in said plurality of dark signals being weighted in sliding fashion.

11. An X-ray diagnostic apparatus as claimed in claim 1 comprising means for producing said dark signal before and after said image signal, and means for forming an arithmetic average of the dark signal obtained before said image signal and the dark signal obtained after said image signal, and wherein said correction means comprises means for controlling said X-ray source and for correcting said image signal dependent on said arithmetic means.

12. An X-ray diagnostic apparatus as claimed in claim 11 wherein said afterglow signal exhibits a decay, and wherein said correction means comprises means for determining said dark signal dependent on said decay of said afterglow signal.

13. An X-ray diagnostic apparatus as claimed in claim 12 comprising means for producing a plurality of image signals including a last image signal and a current image signal and means for producing a plurality of dark images between said last image signal and said current image signal.

* * * * *